(12) United States Patent
Betrabet et al.

(10) Patent No.: US 7,045,028 B2
(45) Date of Patent: May 16, 2006

(54) COMPOSITE AND ABSORBENT ARTICLE COMPRISING ULTRASONICS-FRIENDLY ADHESIVE, AND METHOD OF MAKING SAME

(75) Inventors: Chinmay Suresh Betrabet, Corvallis, OR (US); Davis Dang Hoang Nhan, Greenville, WI (US)

(73) Assignee: Kimberly-Clark Wordwide, Inc., Neenah, WI (US)

( * ) Notice: Subject to any disclaimer, the term of this patent is extended or adjusted under 35 U.S.C. 154(b) by 439 days.

(21) Appl. No.: 10/360,360

(22) Filed: Feb. 6, 2003

(65) Prior Publication Data

US 2003/0120250 A1    Jun. 26, 2003

Related U.S. Application Data

(62) Division of application No. 09/801,526, filed on Mar. 8, 2001, now Pat. No. 6,541,679.

(60) Provisional application No. 60/188,432, filed on Mar. 10, 2000.

(51) Int. Cl.
    *B32B 31/16*    (2006.01)
(52) U.S. Cl. ................................ 156/73.1; 156/325
(58) Field of Classification Search ............... 156/73.1, 156/325, 580.1, 580.2; 264/442, 443, 444, 264/445; 425/174.2
    See application file for complete search history.

(56) References Cited

U.S. PATENT DOCUMENTS

| | | | |
|---|---|---|---|
| 4,595,445 A | 6/1986 | Hombach et al. | |
| 4,610,681 A | 9/1986 | Strohbeen et al. | |
| 4,641,381 A | 2/1987 | Heran et al. | |
| 5,096,532 A | 3/1992 | Neuwirth et al. | |
| 5,110,403 A | 5/1992 | Ehlert | |
| 5,229,456 A | 7/1993 | Ilenda et al. | |
| 5,904,675 A | 5/1999 | Laux et al. | |
| 5,964,973 A | 10/1999 | Heath et al. | |
| 6,287,403 B1 * | 9/2001 | Couillard et al. | 156/73.1 |
| 6,313,569 B1 | 11/2001 | Sawai et al. | |
| 6,521,067 B1 * | 2/2003 | Clark | 156/73.1 |
| 6,541,679 B1 | 4/2003 | Betrabet et al. | |

FOREIGN PATENT DOCUMENTS

WO    WO 99/25296    5/1999

\* cited by examiner

*Primary Examiner*—James Sells
(74) *Attorney, Agent, or Firm*—Gregory E. Croft; Sebastian C. Pugliese (57) ABSTRACT

The present invention is directed to reducing the build up or accretion of adhesive, alone or in combination with other materials, on the surfaces of equipment used to ultrasonically treat a workpiece (e.g., ultrasonically bonding various components or pieces to one another.) Thus the invention encompasses composites, absorbent products, and methods of making said composites and products where an adhesive composition having certain identified properties is used to reduce the build up or accretion of the adhesive on ultrasonic bonding equipment. In one embodiment of the invention, a composite includes an adhesive having a capillary-viscosity value of about 7 Pa·sec or greater and a Shore-OO-Hardness value of about 65 or greater, whereby the relative accretion value is less than about 1, and more particularly less than about 0.5.

2 Claims, 2 Drawing Sheets

COMPOSITE AND ABSORBENT ARTICLE COMPRISING ULTRASONICS-FRIENDLY ADHESIVE, AND METHOD OF MAKING SAME

This application is a divisional of U.S. patent application Ser. No. 09/801,526 filed Mar. 8, 2001, now U.S. Pat. No. 6,541,679 which claims priority from U.S. Provisional Application No. 60/188,432 filed on Mar. 10, 2000.

BACKGROUND OF THE INVENTION

People rely on absorbent articles to help participate in and enjoy their daily activities.

Absorbent articles, including adult incontinence articles and diapers, are generally manufactured by combining a substantially liquid-permeable topsheet; a substantially liquid-impermeable backsheet attached to the topsheet; and an absorbent core located between the topsheet and the backsheet. When the article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core is designed to have desirable physical properties, e.g. a high absorbent capacity and high absorption rate, so that bodily fluids can be transported from the skin of the wearer into the disposable absorbent article.

The topsheet, backsheet, absorbent core, and other components of an absorbent structure or product may comprise discrete layers or nonlayered shapes and configurations. Furthermore, these components or pieces may be coextensive or non-coextensive, depending on the requirements of the product. Generally each of the individual components or pieces is arranged so that it is in intimate contact along at least a portion of its boundary with at least one other adjacent component or piece of the absorbent article or structure. Typically each component or piece is connected to an adjacent portion of the absorbent structure by a suitable bonding and/or fiber entanglement mechanism, such as ultrasonic or adhesive bonding, or mechanical or hydraulic needling.

Thus, as an absorbent structure or product is made, it generally undergoes a number of different steps in which components or pieces are connected to one another. For example, portions of the topsheet and backsheet typically are bonded together. Also, to the extent the absorbent structure or product incorporates elastomeric regions such as elasticized waistbands or elasticized leg bands or leg cuffs, elastic strands or elastic ribbons are typically bonded to a portion of one or more base materials, substrates, or webs.

If an adhesive is used to attach a portion of one component or piece to a portion of another component or piece to form a composite, the adhesive may be exposed to ultrasonic energy in subsequent processing steps if part or all of the composite passes through ultrasonic-treating equipment. The ultrasonic energy may cause the adhesive to flow. This in turn may lead to build up or accretion of the adhesive on parts of the ultrasonic-treating equipment if the adhesive penetrates through some or all of the composite, between separate layers of the composite if the composite is a laminate, or both. This build up or accretion may decrease performance of the ultrasonic-treating equipment, and may lead to increased down time of the production machine.

What is needed is a composite and absorbent article comprising an adhesive that is less susceptible to building up or accreting on the surfaces of ultrasonic-treating equipment, and a method of making such a composite and article.

BRIEF SUMMARY OF THE INVENTION

We have found that an adhesive is less likely to build up or accrete on the surfaces of ultrasonic-treating equipment if the adhesive has a capillary-viscosity value of about 7 Pascal seconds (hereinafter referred to as "Pas·sec") or greater and a Shore-OO-Hardness value of about 65 or greater, and more particularly a capillary-viscosity value of about 9 Pas·sec or greater and a Shore-OO-Hardness value of about 90 or greater. As discussed below, the recited capillary viscosities are reported as real (rather than apparent) viscosities corresponding to a shear rate of 5000 seconds$^{-1}$. Where necessary, these recited viscosities were obtained by interpolation. Shore-OO-Hardness values are reported in units of durometer.

Accordingly, one version of the invention is directed to a composite comprising a first piece and a second piece, a portion of the first piece being bonded to a portion of the second piece using an adhesive composition having a capillary-viscosity value of about 7 Pas·sec or greater and a Shore-OO-Hardness value of about 65 or greater, wherein the relative accretion value is less than about 1, and more particularly less than about 0.5. As defined below, "relative accretion value" is the mass of an adhesive having features of the present invention that accretes or builds up (alone or in combination with other materials) on surfaces of ultrasonic-treating equipment divided by the mass of another adhesive that accretes or builds up (alone or in combination with other materials) on surfaces of ultrasonic-treating equipment (under the same conditions and using the same equipment, with the difference being the identity of the adhesive used). The identity of the adhesive corresponding to the accretion value appearing in the denominator of the relative accretion value is that of a conventional adhesive used to bond pieces together when making a composite. In the examples below, the identity of the adhesive corresponding to the accretion value appearing in the denominator is a hot-melt adhesive composition available under the alphanumeric designator H2096 from Bostik Findley (formerly known as Ato Findley), a business having offices in Wauwatosa, Wis. It should be understood that the relative accretion index serves to quantify a feature of composites and absorbent products of the present invention: when composites or absorbent products of the present invention are processed by ultrasonic-treating equipment, there is less buildup or accretion of adhesive and other materials on the surfaces of the ultrasonic-treating equipment compared to the buildup or accretion that occurs when processing composites or absorbent products incorporating conventional adhesive compositions.

In some versions of the invention, a first piece is not attached to a second piece to form a composite, but instead a single piece is folded over and attached to itself using an adhesive composition having the above-recited properties.

Another version of the invention is directed to a composite comprising a first piece and a second piece, a portion of the first piece being bonded to a portion of the second piece using an adhesive composition having a capillary-viscosity value of about 9 Pas·sec or greater and a Shore-OO-Hardness value of about 90 or greater, wherein the relative accretion value is less than about 0.1, and more particularly less than about 0.05. In some versions of the invention, a first piece is not attached to a second piece to form a composite, but instead a single piece is folded over and attached to itself using an adhesive composition having the above-recited properties.

In another aspect, the invention is directed to a composite having a creep-resistance value of about 30% or greater, specifically about 40% or greater, and particularly about 50% or greater, the composite comprising: a first piece and a second piece; at least one elastic strand or ribbon; and an adhesive composition binding at least a portion of each strand or ribbon to a portion of the first piece and a portion of the second piece, the adhesive composition having a capillary-viscosity value of about 7 Pas·sec or greater and a Shore-OO-Hardness value of about 65 or greater, wherein the relative accretion value is less than about 1, and more particularly less than about 0.5. In some versions of the invention, the elastic strand or ribbon is not attached to a first piece and a second piece to form a composite, but instead is attached to, and enclosed by, a single piece (e.g., by folding over a portion of the single piece over the elastic strand or ribbon to form a composite). "Creep-resistance" refers to the elastic-strand (or elastic ribbon) holding power of a particular system for attaching one or more elastic materials to at least one piece, and is discussed below in more detail.

In another aspect, the invention is directed to a composite having a creep-resistance value of about 30% or greater, specifically about 40% or greater, and particularly about 50% or greater, the composite comprising: a first piece and a second piece; at least one elastic strand or ribbon; and an adhesive composition binding at least a portion of each strand to a portion of the first piece and a portion of the second piece, the adhesive composition having a capillary-viscosity value of about 9 Pas·sec or greater and a Shore-OO-Hardness value of about 90 or greater, wherein the relative accretion value is less than about 0.1, and more particularly less than about 0.05. In some versions of the invention, the elastic strand or ribbon is not attached to a first piece and a second piece to form a composite, but instead is attached to, and enclosed by, a single piece (e.g., by folding over a portion of the single piece over the elastic strand or ribbon to form a composite).

An absorbent product having features of the present invention includes: a liquid-permeable topsheet; a liquid-impermeable backsheet attached to the topsheet; an absorbent core disposed between the topsheet and the backsheet; and a composite as described in any one of the preceding paragraphs, the composite being attached to, or an integral part of, a portion of the topsheet, a portion of the backsheet, or both. It should be understood that the composite may be attached directly, or indirectly through one or more additional pieces or components (i.e., an intermediate piece or component), to the topsheet or backsheet.

One version of a method of making a composite of the present invention comprises the steps of: providing a first piece; providing a second piece; and attaching a portion of the first piece to a portion of the second piece using an adhesive composition having a capillary-viscosity value of about 7 Pas·sec or greater and a Shore-OO-Hardness value of about 65 or greater, wherein the relative accretion value is less than about 1, and more particularly less than about 0.5. In some versions of the invention, a first piece is not attached to a second piece to form a composite, but instead a single piece is provided, and this piece is folded over and attached to itself using an adhesive composition having the above-recited properties.

Another version of a method of making a composite of the present invention comprises the steps of: providing a first piece; providing a second piece; and attaching a portion of the first piece to a portion of the second piece using an adhesive composition having a capillary-viscosity value of about 9 Pas·sec or greater and a Shore-OO-Hardness value of about 90 or greater, wherein the relative accretion value is less than about 0.1, and more particularly less than about 0.05. In some versions of the invention, a first piece is not attached to a second piece to form a composite, but instead a single piece is provided, and this piece is folded over and attached to itself using an adhesive composition having the above-recited properties.

In another aspect, a method having features of the present invention comprises the steps as described in either of the two preceding paragraphs, with the additional step of ultrasonically bonding a portion of the composite (i.e., either the first piece to the second piece, or the folded-over portions of a single piece). Alternatively, or in addition to, this added step, the composite is ultrasonically bonded to a third piece, such as the topsheet, backsheet, or some other part of a disposable absorbent article, as the article is systematically built on a production line.

For example, a method of making an absorbent article or product having features of the present invention includes the steps of: providing a liquid-permeable topsheet; providing a liquid-impermeable backsheet; providing an absorbent core; providing a composite prepared by the steps outlined in one of the two paragraphs before the immediately preceding paragraph; positioning the absorbent core so that it will be between the topsheet and the backsheet in the disposable absorbent article; attaching the backsheet to the topsheet; and attaching a portion of the composite to a portion of the topsheet, a portion of the backsheet, or a portion of both.

Another version of a method of making a composite of the present invention comprises the steps of: providing a first piece; providing a second piece; providing at least one elastomeric strand or ribbon; and attaching a portion of the strand or ribbon to a portion of the first piece and a portion of the second piece using an adhesive composition having a capillary-viscosity value of about 7 Pas·sec or greater and a Shore-OO-Hardness value of about 65 or greater, wherein the relative accretion value is less than about 1, and more particularly less than about 0.5, and wherein the composite has a creep-resistance value of about 30% or greater, specifically about 40% or greater, and particularly about 50% or greater. In some versions of the invention, the elastic strand or ribbon is not attached to a first piece and a second piece to form a composite, but instead is attached to, and enclosed by, a single piece (e.g., by folding over a portion of the single piece over the elastic strand or ribbon to form a composite).

In another aspect, a method of making a composite of the present invention comprises the steps of: providing a first piece; providing a second piece; providing at least one elastomeric strand or ribbon; and attaching a portion of the strand or ribbon to a portion of the first piece and a portion of the second piece using an adhesive composition having a capillary-viscosity value of about 9 Pas·sec or greater and a Shore-OO-Hardness value of about 90 or greater, wherein the relative accretion value is less than about 0.1, and more particularly less than about 0.05, and wherein the composite has a creep-resistance value of about 30% or greater, specifically about 40% or greater, and particularly about 50% or greater. In some versions of the invention, the elastic strand or ribbon is not attached to a first piece and a second piece to form a composite, but instead is attached to, and enclosed by, a single piece (e.g., by folding over a portion of the single piece over the elastic strand or ribbon to form a composite).

In another aspect, a method having features of the present invention comprises the steps as described in either of the two preceding paragraphs, with the additional step of ultrasonically bonding a portion of the first piece to a portion of the second piece, or ultrasonically bonding the folded-over portion of a single piece. Alternatively, or in addition to, this added step, the composite is ultrasonically bonded to a third piece, such as the topsheet, backsheet, or some other part of a disposable absorbent article, as the article is systematically built on a production line.

For example, a method of making an absorbent article having features of the present invention includes the steps of: providing a liquid-permeable topsheet; providing a liquid-impermeable backsheet; providing an absorbent core; providing a composite prepared by the steps outlined in one of the two paragraphs before the immediately preceding paragraph; positioning the absorbent core so that it will be between the topsheet and the backsheet in the disposable absorbent article; attaching the backsheet to the topsheet; and attaching a portion of the composite to a portion of the topsheet, a portion of the backsheet, or a portion of both.

In another aspect, a method of making a composite or disposable absorbent article of the present invention comprises the steps of: providing a candidate adhesive composition; determining the accretion value of the candidate adhesive composition; determining the accretion value of an adhesive composition presently used to make a composite or absorbent product; and selecting the candidate adhesive composition as a substitute for the presently-used composition if the relative accretion value is less than 1, wherein the relative accretion value is determined by dividing the accretion value of the candidate adhesive composition by the accretion value of the presently-used adhesive composition.

In another aspect, a method of making a composite or an absorbent article of the present invention comprises the steps of: providing a candidate adhesive composition; measuring the capillary-viscosity value of the candidate adhesive composition; measuring the Shore-OO-Hardness value of the candidate adhesive composition; and selecting the candidate adhesive composition for use in making the composite or disposable absorbent article if the candidate adhesive has a capillary-viscosity value of about 7 Pas·sec or greater and a Shore-OO-Hardness value of about 65 or greater, and more particularly a capillary-viscosity value of about 9 Pas·sec or greater and a Shore-OO-Hardness value of about 90 or greater.

In another aspect, a method of making a composite or disposable absorbent article of the present invention comprises the steps of: providing a candidate adhesive composition; measuring the capillary-viscosity value of the candidate adhesive composition; measuring the hardness of the candidate adhesive composition; and selecting the candidate adhesive composition as a substitute for another adhesive composition used in constructing a composite or disposable absorbent article if the measured capillary-viscosity value and hardness value of the candidate adhesive composition correspond to a relative accretion value less than 1, wherein the relative accretion value is determined by dividing the accretion value of the candidate adhesive composition by the accretion value of the substituted-for adhesive composition.

These and other features, aspects, and advantages of the present invention will become better understood with regard to the following description, appended claims, and accompanying drawings.

DETAILED DESCRIPTION OF THE INVENTION

The present invention is directed to reducing the build up or accretion of adhesive, alone or in combination with other materials, on the surfaces of ultrasonic-treating equipment, e.g. equipment used to ultrasonically bond various components or pieces to one another. Thus the invention encompasses composites, absorbent products, and methods of making said composites and products, wherein an adhesive composition having certain identified properties is used to help build the composite or product while reducing build up or accretion of the adhesive on ultrasonic-treating equipment.

Before describing various embodiments having features of the present invention, it is useful to define certain terms for purposes of the present application.

"Bonded" or "attached" refers to the joining, adhering, connecting, or the like, of two elements. Two elements are considered bonded together when they are bonded directly to one another or indirectly to one another (e.g., as when each element is directly bonded to an intermediate element).

"Piece" or "component," as used herein, means a discrete part, a web, or some other element used to help build a composite or an absorbent product. Examples of such discrete parts or webs are discussed below.

"Elastic strand," as used herein, comprises polymeric constituents such as, but not limited to: polyester; polyurethane; polyether; polyamide; polyacrylate; or combinations thereof, including random, block, or graft copolymers such as polyester-b-polyurethane block copolymers, polyether-b-polyurethane block copolymers, styrenic block copolymers, and/or polyether-b-polyamide block copolymers. Examples of elastic strand include LYCRA, a multifilament elastomeric thread sold by E. I. Du Pont de Nemours and Company, a business having offices in Wilmington, Del., and GLOSPAN, an elastic strand made by Globe Manufacturing Company, a business having offices in Fall River, Mass.

The present invention is directed to composites and disposable absorbent products made with or with out one or more elastomeric strands or ribbons. For those composites comprising an elastic strand, elastic ribbon, or other elastomeric material, "creep-resistance" or "creep-resistance value" refers to the elastic-strand holding power of a particular system for attaching one or more elastic materials to at least one piece. For example, if an adhesive is applied in liquid form to a first piece, and an elastic strand or strands are then pressed against the adhesive and first piece to attach the strand or strands to the first piece, then creep resistance is a measure of the quality of the adhesive bond between the strand or strands and the first piece. Generally the elastic strand or strands will be sandwiched between a first piece and a second piece, or will be enclosed by folding a piece over the strands.

The term "nonwoven" or "nonwoven web" refers to a web of material that is formed without the aid of a textile weaving or knitting process. The term "fabrics" is used to refer to all of the woven, knitted, and nonwoven fibrous webs.

A "liquid-permeable topsheet" generally comprises a nonwoven web; a spunbond, meltblown, or bonded-carded web composed of synthetic polymer filaments or fibers, such as polypropylene, polyethylene, polyesters or the like; a perforated film; or a web of natural polymer filaments or fibers such as rayon or cotton. In addition, the topsheet may be treated with a surfactant to aid in fluid transfer.

A "liquid-impermeable backsheet" generally comprises moisture-barrier materials such as films, wovens, nonwovens, laminates of films, or the like. For example, the backsheet may comprise a substantially liquid-impermeable web or sheet of plastic film such as polyethylene, polypropylene, polyvinyl chloride, or similar material.

As discussed above, the present invention is directed to composites and absorbent products comprising an adhesive that is less susceptible to building up on the surfaces of ultrasonic-treating equipment, as well as methods for making said composites and products. Descriptions of exemplary versions of composites and/or absorbent articles serve to illustrate the present invention.

Some disposable absorbent articles are constructed with various types of elasticized waistbands and elasticized leg bands or leg cuffs. One method of constructing elasticized regions is to incorporate elastic strands into a laminate that is then attached to a part of the disposable absorbent product as it is built. For example, elastic strands have been laminated between layers of polymer film and/or layers of woven or nonwoven fabrics to provide the absorbent product with elastomeric regions. Folded-over layers have also been employed to enclose or envelop selected strands of material. These folded-over layers have been employed to enclose elastomeric strands within the waistband, leg cuff and inner barrier cuff components of disposable diapers and other disposable absorbent articles. The polymeric film or films, layers of woven or nonwoven fabrics, and/or folded-over layers may be an integral portion of the topsheet and/or backsheet discussed above, or may be separate components that are attached to the topsheet and/or backsheet.

In order to introduce an elastic strand to the product being made, a spool of the strand is generally placed on an unwind stand. The strand is then continuously unwound, in the machine direction, with the strand being attached to a substrate, such as a base layer of material, to provide a composite. For purposes of this application, "piece" or "component" encompasses webs such as the aforementioned substrates or base layers of materials. As stated above, examples of a base material include, but are not limited to, polymeric films and/or woven or nonwoven fabrics. Also, as stated above, the elastic strand is typically sandwiched between two different layers of base material, or between a folded-over portion of base material, to form a composite. In many cases the strand is attached to the base material, or materials, using an adhesive.

To produce an elasticized region, the strand is stretched when it is attached to a base material to form a substrate composite. The stretched elastic strands tend to retract and gather the composite, thereby imparting elastomeric properties to the composite. As mentioned above, the composite may be formed to provide an elasticized waistband or leg band in a disposable absorbent product.

Thus, for example, a co-pending application corresponding to PCT International Publication Number WO 99/25296, published on 27 May 1999 and entitled "Disposable Underpants," and which is hereby incorporated by reference in a manner consistent with the present application, discloses a disposable underpant comprising elasticized leg and waist openings. The published application discloses the attaching of one or more elastic members, such as elastic strands, threads, or ribbons, to a substrate, web, or other piece to form a composite that functions as an elasticized waist opening. (See generally page 6, lines 6–34, of to PCT International Publication Number WO 99/25296.) In one embodiment, the published application discusses the sandwiching of elastic members between an outer cover and a body liner to form the composite. (Id. at page 18, line 30 through page 19, line 5.) Details regarding the nature of the elastic members, and how they may be attached to components or pieces such as an outer cover or body liner—as these terms are used in this PCT publication—are generally described from page 19, line 17, through page 21, line 6 of this referenced PCT publication. The publication discloses the use of an adhesive, typically applied in a meltblown or swirl pattern, to bond the elastic material (e.g., one or more elastic strands) to one or more pieces (in this case to the outer cover and body liner, as these terms are used in the publication) to form a composite that functions as an elasticized waist opening. The publication further discloses an adhesive that may be used for this purpose: a hot-melt adhesive designated as H2096 from Ato Findley Adhesives, a business having offices in Milwaukee, Wis.

Similarly, this publication discusses the making of composites that function as elastic waist or crotch openings in a disposable underpant. (See generally page 21, line 6, through page 26, line 5.) The adhesive identified above is also given as an example of an adhesive that may be used to make elastic waist or crotch openings.

In subsequent processing steps, some portion of the composite or absorbent product may be processed using ultrasonic bonding equipment. After exemplary composites such as those referred to above are formed using an adhesive, some or all of the composite may be exposed to ultrasonic energy. Again referring to PCT International Publication Number WO 99/25296, the publication discloses the use of ultrasonic bonding to form side seams or seals in the disposable underpant. (See, e.g., page 29, lines 10–25; additional detail regarding the forming of such side seals is disclosed in U.S. Pat. No. 4,610,681, which issued on 9 Sep. 1986 and is entitled "Disposable Underpants Having Discrete Outer Seals," and which is hereby incorporated by reference in a manner consistent herewith; and U.S. Pat. No. 4,641,381, which issued on 10 Feb. 1997 and is entitled "Disposable Underpants, Such as Infant's Training Pants and the Like," which is also incorporated by reference in a manner consistent with the present application.) Thus adhesive used to make composites functioning as elasticized waist openings, elasticized leg openings, or both, is exposed to ultrasonic energy when ultrasonic-bonding equipment is used to form the seams or seals in the disposable absorbent article.

The ultrasonic energy may cause the adhesive used to attach elastic materials, such as an elastic strand or ribbon, to a piece, such as a nonwoven web, to flow. The flowing adhesive may then penetrate through the piece to contact the surfaces of ultrasonic-bonding equipment. Alternatively, or in addition to, this mechanism, the adhesive may flow through gaps between a laminate structure, if the elastic material is sandwiched between two pieces or is enclosed by a single piece, and build up on the surface of the ultrasonic-bonding equipment. This in turn may lead to build up or accretion of adhesive on parts of the ultrasonic-bonding equipment. As the adhesive builds up, the adhesive may bind other materials such that the build up or accretion comprises both adhesive and other materials, such as fibers from a nonwoven web or other component or piece. This build up or accretion may decrease performance of the ultrasonic-bonding equipment, and may lead to increased down time of the production machine used to make the substrate composite and/or absorbent product.

To solve this problem we have identified certain properties that reduce or minimize build up or accretion of an adhesive on ultrasonic-bonding equipment. By choosing an adhesive formulation having recited values for capillary viscosity and hardness, accretion or build up of the adhesive is reduced. (See discussion below in the Examples section.) Thus, in the above example, an adhesive composition having a capillary-viscosity value of about 7 Pas·sec or greater and a Shore-OO-Hardness value of about 65 or greater, and more particularly a capillary-viscosity value of about 9 Pas·sec or greater and a Shore-OO-Hardness value of about 90 or greater, would be used to bond elastic material to the outer cover and body liner in order to form a composite that functions as an elasticized waist opening.

In another version of the invention, a region of an elastomeric composite comprising an adhesive is exposed to ultrasonic energy to "kill" or otherwise deaden the elasticity or contractability in these regions. For example, U.S. Pat. No. 5,904,675, which is entitled "Absorbent Article with Improved Elastic Margins and Containment System," and is hereby incorporated by reference in a manner consistent herewith, discusses the use of ultrasonic energy to deaden the elasticity of selected regions of a composite comprising elastic members (e.g., strands of elastic material). (See col. 18, lines 1–18 of U.S. Pat. No. 5,904,675.) To the extent such elastomeric composites are made by adhesively bonding elastic members to one or more pieces or components (e.g., a nonwoven web or webs), ultrasonic energy used to produce a "deadened" region relative to contractability may cause the adhesive to flow, thereby leading to a build up or accretion on ultrasonic bonding equipment. As discussed above, use of an adhesive having certain properties will reduce or eliminate such buildup or accretion. Thus, in one embodiment, an adhesive composition having a capillary-viscosity value of about 7 Pas·sec or greater and a Shore-OO-Hardness value of about 65 or greater, and more particularly a capillary-viscosity value of about 9 Pas·sec or greater and a Shore-OO-Hardness value of about 90 or greater, would be used to bond elastic members when forming an elastomeric composite before certain regions of the composite were "deadened" relative to contractability using ultrasonic energy.

In another aspect, adhesive having recited properties of capillary viscosity and hardness is used to attach one piece or component to another piece or component to form a composite, with some or all of the composite then being exposed to ultrasonic energy. For example, U.S. Pat. No. 5,904,675 (which, as discussed above, is incorporated by reference in a manner consistent herewith) discloses an absorbent article in which a fastener tab may be adhesively bonded to a panel member, and, if desired, ultrasonically bonded to provide supplemental bonding. (See generally col. 37, lines 4–14 of U.S. Pat. No. 5,904,675.) Alternatively, elasticized legband barrier flaps, such as containment flaps, may be ultrasonically bonded directly or indirectly to another component or piece, such as a topsheet. (See, e.g., col. 6, lines 57–61 of U.S. Pat. No. 5,904,675.) If a piece is first bonded to another piece, and then exposed to ultrasonic energy to produce a supplemental bond, then the adhesive may flow, leading to build up or accretion on ultrasonic bonding equipment. Accordingly, in this particular example, use of an adhesive composition having a capillary-viscosity value of about 7 Pas·sec or greater and a Shore-OO-Hardness value of about 65 or greater, and more particularly a capillary-viscosity value of about 9 Pas·sec or greater and a Shore-OO-Hardness value of about 90 or greater, to bond a first piece to second piece would reduce or eliminate build up or accretion on ultrasonic-bonding equipment when the composite was exposed to ultrasonic energy.

In another aspect, a method of the present invention involves evaluating one or more candidate adhesives as possible replacements for another adhesive used to make a composite or absorbent article, with the goal being to reduce or eliminate build up or accretion of adhesive (with or without other materials, such as individual fibers) on ultrasonic-treating equipment. Typically the evaluation will involve determining the amount of build up or accretion on ultrasonic-treating equipment over a fixed time period for a given adhesive (here identified as the first adhesive). Then the build up or accretion of one or more candidate adhesives is determined under the same conditions. By comparing the accretion value of the first adhesive with the accretion values of the candidate adhesives, ultrasonics-friendly adhesives (i.e., adhesives that will reduce or eliminate build up on ultrasonic-treating equipment) may be identified. Alternatively, the candidate adhesives are evaluated by measuring the capillary-viscosity values and Shore-OO-Hardness values of the candidates. Those candidate adhesives having a capillary-viscosity value of about 7 Pas·sec or greater and a Shore-OO-Hardness value of about 65 or greater, and more particularly a capillary-viscosity value of about 9 Pas·sec or greater and a Shore-OO-Hardness value of about 90 or greater, are selected as potential replacements for another adhesive used to make a composite or absorbent article.

In yet another approach, candidate adhesives are evaluated by measuring capillary-viscosity values and hardness values of the candidates. Those candidates adhesives having a capillary-viscosity value and hardness value corresponding to a relative accretion value less than 1, wherein the relative accretion value is determined by dividing the accretion value of the candidate adhesive by the accretion value of another adhesive used to make a composite or absorbent product, are selected as possible replacements for the other adhesive. One example of a method of evaluating candidate adhesives as possible replacements for another adhesive used to make composites or absorbent products in order to reduce build up or accretion on ultrasonic-treating equipment is described in the Examples section below.

The above examples and versions are provided to illustrate the invention. It should be understood that the present invention is not limited to these particular embodiments, but covers other processes, composites, and products where an adhesive is used to help make a composite or absorbent product, with the adhesive subsequently being exposed to ultrasonic energy such that the adhesive may build up or accrete on the surface or surfaces of ultrasonic-treating equipment.

TESTS

Creep Resistance

Figure 1:
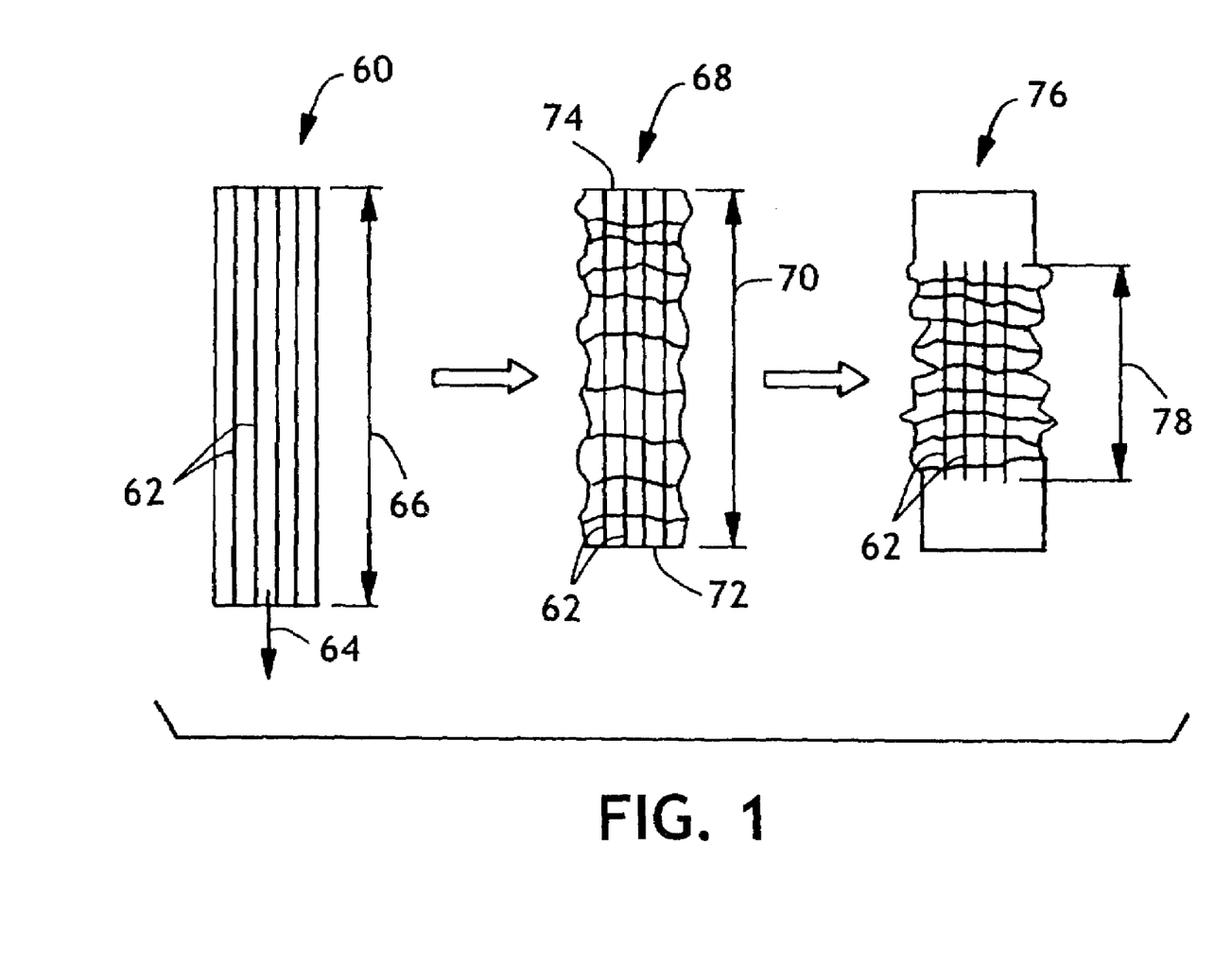
FIG. 1 gives sequential views of a composite as it undergoes one version of a test for creep.

An explanation of a test for measuring creep provides additional detail regarding this concept. As discussed below, substrate composites were formed by sandwiching a plurality of elastic strands between two base materials to form a substrate composite or laminate. As depicted in FIG. 1, a sample 60 having a width of 60 millimeters and a length of 250 millimeters was cut from a continuous web of the substrate composite. The composite incorporated 6 elastic strands 62, in two groupings of 3 (not all strands are depicted, and their locations in FIG. 1 are for illustrative purposes only, and do not correspond to the groupings described in the text). The groupings were 10 millimeters apart; within a grouping the strands were approximately 5 millimeters apart. To conduct the test for measuring creep, the sample was first fully extended by hanging the sample vertically in front of an illuminated light box. The top of the sample was clamped to the light box and a 1000-gram weight was clamped to the bottom of the sample (the arrow 64 denotes the effect of the weight). In this fully extended form, a template was used to mark the substrate near the opposing ends to denote a 200 millimeter length 66 (sample material beyond the 200 mm length is not depicted).

The weight was then removed and the sample was placed horizontally on a piece of cardboard. The substrate composite 68 was allowed to contract so that the marks on the substrate composite were now 175 millimeters apart 70 (again, sample material beyond the 175 mm length is not depicted). The sample was then stapled to the cardboard, with the staples (not shown) located outside the 175 mm length. The lines parallel to the length dimension of the sample in this partially retracted form, i.e. 175 mm, represent the elastic strands 62 (not all strands are depicted), with the exception of the outermost lines, which represent the edges of the substrate composite. The lines that are perpendicular to the length dimension of the substrate composite represent gathers of base material caused by the elastomeric strands retracting after the weight was removed (except for the outermost lines that are perpendicular to the length dimension, which again represent marks on the substrate composite that are 175 mm apart). When the elastic strands retract, they gather base material so that the substrate composite itself has elastomeric qualities.

The elastic strands were then cut at the marks 72 and 74 denoting the length of 175 mm. Because the strands were located between two base materials, typically one of the base materials was partially or completely slit when the strands were cut. After the elastic strands 62 were cut, they generally retracted. About 1–2 minutes after the strands were cut, the length of the retracted strands was measured. The difference between 175 mm and the initial retracted strand length 78, or $I_{initial}$, was used to calculate the "initial creep" of the sample. For the present application, initial creep is calculated using the following equation:

Initial Creep, in percent=[(175 mm−$I_{initial}$ mm)÷175 mm]100       [Eq. 1]

After initial creep of the sample was determined, the substrate composite 76—still stapled to the cardboard—was placed in a forced-air oven pre-heated to a temperature of 100° F. After 90 minutes, the substrate composite and cardboard were removed from the oven. The substrate composite was then allowed to cool for approximately 10 minutes. The length of the strands, which now had retracted still more, was measured.

The difference between 175 mm and the final retracted length, or $Y_{final}$, was used to calculate the "final creep" of the sample. For the present application, final creep is calculated using the following equation:

Final Creep, in percent=[(175 mm−$Y_{final}$ mm)÷175 mm]100       [Eq. 2]

Creep resistance, or the creep-resistance value, for purposes of the present application, is calculated as follows:

Creep Resistance, in percent=100−Final Creep       [Eq. 3]

For disposable absorbent articles that are worn near the body of the wearer, final creep provides a measure of performance of the article during use, since the human body temperature is about 98° F. Hypothetical situations provide more detail on the meaning of this measurement. Assume that a substrate composite is made in which three elastic strands are sandwiched between two base materials or one folded-over base material. Also assume that the laminate is made by attaching the strands to a base material using an adhesive while the strands are in elongated form, typically at an elongation from about 200% to about 300% (see Examples below and U.S. Pat. No. 5,964,973, entitled "Method and Apparatus for Making an Elastomeric Laminate Web," which is hereby incorporated by reference in a manner consistent with the present specification, for more detail on how a substrate composite incorporating elastic strand is made). If, after aging at 100° F. for 90 minutes, the elastic strands detach from the adhesive and base material along most of the length of each strand, and the strands retract, then final creep will be relatively high and creep resistance will be relatively low. Performance of the substrate composite as an elastomeric composite will likely be poor because the detached strands, now retracted and embodying less tension, are less likely to gather the base material or materials in a relatively uniform fashion along the length of the substrate composite, if at all.

In a second hypothetical situation, assume again that a substrate composite is made as described in the preceding paragraph. Assume also that the strands are attached to the base material or materials using an adhesive. If, after aging at 100° F. for 90 minutes, the elastic strands remain uniformly attached to the base material along most of the length of each strand, then final creep will be relatively low and creep resistance will be relatively high. Performance of the substrate composite as an elastomeric composite will likely be good because the strands will retract and gather the base material or materials in a relatively uniform fashion along the length of the substrate composite.

Capillary Viscosity

The instrument used to determine capillary viscosity was a Goettfert Rheograph 2003, obtained from Goettfert, a business having offices in Rock Hill, S.C. (The accompanying manual for this device is designated Rheograph 2003; Rev. 0, 30.08.94. The manual for the accompanying WinRHEO software is designated WinRHEO; Rev. 0; 28.03.94. The WinRHEO software installed on the equipment was version 2.55. Both manuals are incorporated by reference in a manner consistent with the present application. The Rheograph 2003 has the following additional specifications: Com #34680; Ser# 48578; Type 13.01; EPROM version 2 13/2.5/2.10.)

Capillary viscosity was determined in the following manner. Because the tested adhesives typically were obtained as chunks or blocks, the adhesive had to be cut into thin slices using a heated wire. About 200 to 400 grams of adhesive cut in this way were placed into a metal can having a diameter of 4 inches and a length of 5 inches. The can was then placed in a forced-air oven (a VWR Hafo series 1670, available from VWR, a business having offices in South Plainfield, N.J.) pre-heated to a temperature of 180° C. At this temperature, the adhesive took approximately two hours to melt. After the time required to melt the adhesive had elapsed, the molten adhesive was poured into a barrel 80 on the capillary-viscosity testing device (see FIG. 2). A piston or plunger (not shown) was used to force the molten adhesive into the barrel while allowing air trapped between the capillary die block 81 and the adhesive to rise and escape through the opening at the top of the barrel. During this adhesive-loading step, the adhesive was pushed into the barrel, but not through the capillary die 82. This loading procedure typically had to be repeated 2–3 times so that the barrel contained sufficient adhesive for the test, which was typically about 20 to 23 grams. This adhesive loading process generally took about 15 minutes. After a sufficient amount of molten adhesive had been transferred from the metal can to the barrel of the capillary-viscosity tester, the sample was allowed to cool in the barrel for approximately 15 minutes before starting the test.

Figure 2:
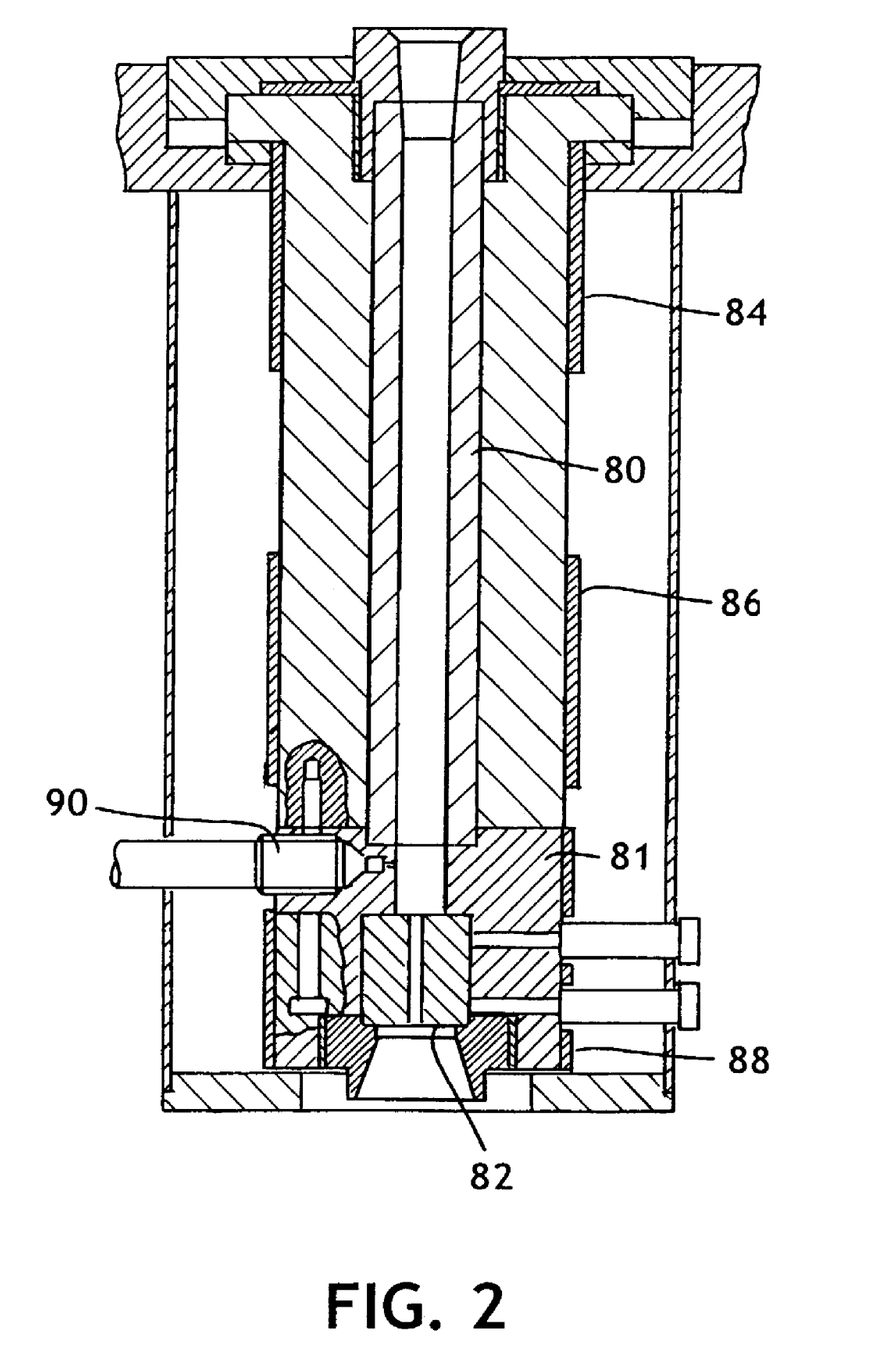
FIG. 2 shows a sectional view of one apparatus for measuring capillary viscosity.

The test conditions were as follows. The capillary die itself comprised a round hole having a diameter of 1 mm, a length of 30 mm (which was also its active length), and a run angle of 180 degrees. The piston, or plunger, had a diameter of 12 mm, which was slightly less than the diameter of the barrel, and a length of 285 mm. The piston fit snugly inside the barrel. The barrel itself was divided into 3 heating zones 84, 86, and 88. Each of these heating zones was individually controllable; all were set to a temperature of 150° C. The pressure transducer 90 that was used to measure pressure had a specification/part number of PBEF 500-34968/400/100; 500 bar. The apparent shear rates that were selected for each test were (in units of reciprocal seconds): 100, 200, 500, 1000, 2000, and 5000. These inputted values served to control the downward movement of the piston through the barrel. The downward movement of the piston generated hydraulic pressure, which forced adhesive through the capillary die. The pressure transducer measured pressure as a function of shear rate. A plot of viscosity versus shear rate was then calculated by the WinRheo software accompanying the Goettfert Rheograph on a general-purpose computer associated with the capillary viscometer. The viscosities at a shear rate of 5000 $s^{-1}$ were obtained by interpolating between data points obtained from the plot of viscosity versus shear rate using an interpolation function in the EXCEL spreadsheet program of Microsoft Office software obtained from Microsoft Corporation, a business having offices in Redmond, Wash.

Hardness

The instrument used to determine hardness was a Shore-OO-Hardness tester made by Shore Instrument and Manufacturing Company, a business having offices in Freeport, N.Y. The hardness tester was checked for accuracy using the gauge supplied with the instrument (reference number 101747.) The upper surface of a block of adhesive, wrapped in release paper, was smoothened by pressing a heated iron against the release paper and the underlying block of adhesive. The block generally had a thickness of at least about 1 inch. The adhesive was then allowed to cool to ambient conditions (about 72° F./40% relative humidity) for about half an hour. After the release paper was removed, the tester was placed on the smoothened surface (i.e., the surface that was ironed with release paper disposed between the surface of the iron and the surface of the block). Hardness was measured five seconds after contact between the sensing tip of the tester with the adhesive surface. Ten observations of hardness were made at different, randomly-chosen points on the surface of the adhesive. The average of the ten observations was reported.

It should be understood that other durometer scales may be used to characterize the hardness of the adhesive.

Relative Accretion Value

The relative accretion or build-up of an adhesive, alone or in combination with other materials—e.g., fibers, was measured by running a laminate of the adhesive and spunbond layers through a rotary ultrasonic bonder at 300 feet per minute for ten minutes. The rotary bonder included a horn and a dot-pattern anvil design. The ultrasonic generator was a 3005 Autotrac, 20 KHz, 3000 watt generator from Dukane Corporation, a business having offices in Saint Charles, Ill. A variable-power supply was used to vary power available to the generator. The power level used was 100%, which corresponded to an ultrasonic wave amplitude of 2.8 to 3.5 mil (1 mil is equivalent to $\frac{1}{1000}$ inch). The horn diameter was approximately 6.75 inches, with the pressure exerted by the horn on the anvil typically about 40 pounds per square inch or more to ensure good contact between the substrate, web, or laminate being processed; the horn; and the anvil.

The anvil had a dot pattern, with each pin having a 45 mil diameter and a height of 31 mil. The spacing between each pin was about 79 mil. The anvil pins were made from D2 tool steel, which was heat treated and through hardened to Rockell C 60–63. The width of the pattern was 300 mil. The diameter of the anvil was about 5.7 inches.

Additional detail on related designs and specifications pertaining to ultrasonic equipment is found in U.S. Pat. Nos. 5,110,403 and 5,096,532, both of which are incorporated by reference in a manner consistent with the present application.

The build-up, which consisted of adhesive and nonwoven fibers, was scraped from the horn and the anvil and weighed, giving the accretion value for the evaluated adhesive.

The laminate was prepared by meltblowing adhesive to get a 10 gram-per-square-meter coverage on a 0.55 ounce-per-square-yard spunbond nonwoven facing. It was applied to one facing and laminated to the other. Typical lamination speeds were 100 feet per minute. Additional detail on preparation of these laminates is given below. (Note: the discussion below presents steps for forming laminates comprising elastic strands. For purposes of measuring accretion values, laminates were made without elastic strands.)

A control laminate made using H2096 adhesive was run through the ultrasonic-bonding equipment and the accretion or build up measured. Then laminates made in the same way, but with other candidate adhesives substituted for the H2096 adhesive, were run through the ultrasonic-bonding equipment and the accretion or build up measured. The relative-accretion value was calculated by dividing the accretion value of the laminate comprising the H2096 adhesive by the accretion value of each laminate comprising a candidate adhesive.

EXAMPLES

Example 1

Composites were made on equipment available form Nordson Corporation, a business having offices in Atlanta, Ga. Each of the bobbins was placed on an unwind stand. Individual strands from the bobbins were directed to a nip between two rolls, a rubber roll having a 4-inch diameter, and a steel roll having a 6-inch diameter. A base material, in this case a nonwoven web, was directed from its corresponding unwind stand to the surface of the steel roll and through the nip. A second nonwoven web was directed from its unwind stand to the surface of the rubber roll and through the nip. Both nonwoven webs comprised fibers of spunbonded polypropylene at a basis weight of 0.55 ounces per square yard. Typically the equipment was operated at a speed of 200 feet per minute.

The elastomeric strands, in this case Lycra 940 decitex, were directed from their corresponding unwinds stands through a comb and toward the nip so that the elastic strands would be sandwiched between the two nonwoven webs. The comb served to provide and maintain the desired crossmachine-directional distribution of the strands. The strands were positioned so that they were about 5 mm from one another across the width of the base materials, in this case nonwoven webs. There were a total of six strands in two sets of three (with the two groupings 10 mm apart).

The speed of the strand unwind stands relative to the speed of the steel and rubber rolls was such that the strands were elongated about 250% when attached to the nonwoven webs using an applied adhesive. The applied adhesives included various adhesives from Ato Findley, a business having offices located in Wauwatosa, Wis. For purposes of determining creep resistances, tested adhesives included those having the following alpha-numeric designators: HX2717-22; HX2717-08; H2525A; and H2096. Each adhesive was applied at a level of addition of 5 g m$^{-2}$ using a swirl spray application method. The adhesive melt tank temperature was set at 370° F. and the air temperature for the swirl application was set at 410° F. The air pressure was 12 psi.

The applicator used to deposit the adhesive was positioned so that the face of the nozzle—which was roughly parallel to the surface of the web to which adhesive was first applied—was 3 inches from the surface of the web. Furthermore, the central axis of the nozzle, which is perpendicular to the web to which adhesive is first applied, was 8 inches from a parallel axis that passes through the nip defined by the rubber and steel rolls. The gauge pressure was set at 40 psi. The adhesive was sprayed on the Lycra which traveled approximately 1 inch above one of the substrates. The other substrate was brought into contact with the Lycra and the underlying substrate at the nip.

Example 2

Composites were made using the procedure and materials outlined in Example 1. Creep resistance was then measured for each of the resulting composites. The results of these measurements are as follows: the composite comprising the H2525 adhesive exhibited a creep resistance of 48%; the composite comprising the HX2717-08 adhesive exhibited a creep resistance of 50%; the composite comprising the HX2717-22 adhesive exhibited a creep resistance of 76%; and the composite comprising the H2096 adhesive exhibited a creep resistance of 64%.

Example 3

Composites made without an elastic material were prepared on equipment available form Nordson Corporation, a business having offices in Atlanta, Ga. Two nonwoven webs comprising spunbonded polypropylene at a basis weight of 0.55 ounces per square yard were directed to a nip between two rolls, a rubber roll having a 4-inch diameter, and a steel roll having a 6-inch diameter. Typically the equipment was operated at a speed of 100 feet per minute.

Various adhesives were applied using a meltblowing technique at an addition rate of 10 grams per square meter. The applied adhesives included various adhesives from Ato Findley, a business having offices located in Wauwatosa, Wis. For purposes of determining relative accretion values, the tested adhesives included those having the following alpha-numeric designators: H9220; H9274; HX2717-22; HX2717-08; H2695-01; H2525A; and H2096. The adhesive melt tank temperature was set as follows: H2096—370° F.; H2525A—330° F.; HX2717-08—360° F.; HX2717-22—350° F.; H9220—360° F.; H2695—380° F.; H9274—360° F. The air temperature was set at 50 degrees higher than the adhesive melt tank temperature. The air pressure was 18 psi.

The applicator used to deposit the adhesive was positioned so that the face of the outlet—which was roughly parallel to the surface of the web to which adhesive was first applied—was 3 inches from the surface of the web. Furthermore, the central axis of the outlet, which is perpendicular to the web to which adhesive is first applied, was 8 inches from a parallel axis that passes through the nip defined by the rubber and steel rolls. The gauge pressure was set at 40 psi. The adhesive was applied to one nonwoven web. The other nonwoven web was brought into contact with the adhesive and the underlying web at the nip.

Example 4

Composites were made using the procedure and materials outlined in Example 3. The capillary-viscosity values, Shore-OO-Hardness values, and relative-accretion values were determined for each of the composites, with the results presented below:

| Adhesive | Capillary Viscosity [Pas · sec] | Shore-OO-Hardness | Relative Accretion Value |
| --- | --- | --- | --- |
| H2096 | 6.6 | 47 | 1 |
| H2525A | 4.9 | 36 | >3 |
| H2695-01 | 10.2 | 55 | 1.5 |
| HX2717-08 | 9.3 | 94 | 0.01 |
| HX2717-22 | 7.4 | 67 | 0.3 |
| H9274 | 3.8 | 95 | 2.9 |
| H9220 | 5.4 | 91 | >2 |

As can be seen from the preceding table, the adhesives having the alpha-numeric designators HX2717-08 and HX2717-22 both have capillary-viscosity values and Shore-OO-Hardness values such that their corresponding relative-accretion values are less than 1. Furthermore, as shown in Example 2, these adhesives, when used to make composites incorporating elastic material, effect creep resistances of about 50% or greater.

Although the present invention has been described in considerable detail with reference to certain versions, other versions are possible. The spirit and scope of the appended claims should not be limited to the description of specific embodiments contained herein.

What is claimed is:

1. A method of making an absorbent product, the method comprising the steps of:

providing a first piece;

providing a second piece; and attaching at least a portion of the first piece to at least a portion of the second piece using an adhesive composition;

wherein the adhesive composition has a capillary-viscosity value of about 9 Pas·sec or greater and a Shore-OO-Hardness value of about 90 or greater;

exposing at least a part of the composite to ultrasonic energy in a subsequent processing step; and before, during or after the processing step in which at least a part of the composite is exposed to ultrasonic energy, attaching at least a portion of the composite to at least a portion of a backsheet, a topsheet, or portions of both a backsheet and a topsheet.

2. A method of making an absorbent product, the method comprising the steps of:
 providing a first piece;
 providing a second piece;
 providing at least one elastomeric strand or elastomeric ribbon; and
 attaching at least a portion of the strand or ribbon to at least a portion of the first piece and at least a portion of the second piece using an adhesive composition;
 wherein the adhesive composition has a capillary-viscosity value of about 9 Pa·sec or greater and a Shore-OO-Hardness value of about 90 or greater, and wherein the creep-resistance value is about 30% or greater;
 exposing at least a part of the composite to ultrasonic energy in a subsequent processing step;
 and before, during, or after the processing step in which at least a part of the composite is exposed to ultrasonic energy, attaching at least a portion of the composite to at least a portion of a backsheet, a topsheet, or portions of both a backsheet and a topsheet.

* * * * *